(12) United States Patent
Andersen (10) Patent No.: US 10,460,836 B2
(45) Date of Patent: Oct. 29, 2019

(54) MEDICAL DEVICE SYSTEM AND METHOD FOR ESTABLISHING WIRELESS COMMUNICATION

(71) Applicant: MEDICOM INNOVATION PARTNER A/S, Struer (DK)

(72) Inventor: Bjørn Knud Andersen, Struer (DK)

(73) Assignee: MEDICOM INNOVATION PARTNER A/S, Struer (DK)

( * ) Notice: Subject to any disclaimer, the term of this patent is extended or adjusted under 35 U.S.C. 154(b) by 726 days.

(21) Appl. No.: 15/139,891

(22) Filed: Apr. 27, 2016

(65) Prior Publication Data

US 2016/0239610 A1  Aug. 18, 2016

Related U.S. Application Data

(63) Continuation of application No. PCT/DK2015/000001, filed on Jan. 5, 2015.

(30) Foreign Application Priority Data

Jan. 8, 2014  (DK) .................................. 2014 00005
Mar. 26, 2014  (DK) .................................. 2014 00175

(51) Int. Cl.
   *G16H 10/65*     (2018.01)
   *A61M 5/32*      (2006.01)
   (Continued)

(52) U.S. Cl.
   CPC ............ *G16H 10/65* (2018.01); *A61M 5/142* (2013.01); *A61M 5/1626* (2013.01); *A61M 5/20* (2013.01);
   (Continued)

(58) Field of Classification Search
   None
   See application file for complete search history.

(56) References Cited

U.S. PATENT DOCUMENTS

2005/0102167 A1   5/2005  Kapoor
2005/0272516 A1*  12/2005  Gobush .............. A63B 24/0003
                                                              473/200
(Continued)

FOREIGN PATENT DOCUMENTS

WO    WO2007/027660 A2    3/2007

OTHER PUBLICATIONS

International Search Report for PCT Patent App. No. PCT/DK2015/000001 (dated Jun. 23, 2015).

*Primary Examiner* — Mohammed Rachedine
(74) *Attorney, Agent, or Firm* — Cermak Nakajima & McGowan LLP; Adam J. Cermak (57) ABSTRACT

A system (20) for establishing wireless communication between at least one medical device (2) having a predefined unique identification (ID) and at least one communication unit (4, 6, 8) includes a communication unit (4, 6, 8) provided with a primary two-way wireless data communication interface (52) including systems for wirelessly performing primary two-way data communication, including receiving and transmitting information (10, 14). The system (20) includes systems for securing that the primary two-way wireless data communication can be carried out if and only if the communication unit (4, 6, 8) positively and in advance has identified the predefined unique identification (ID) of the medical device (2). The system (20) includes secondary one-way wireless communication systems (24, 24', 28, 30) configured for carrying out identification of the predefined unique identification (ID) of the medical device (2) through secondary wireless communication.

12 Claims, 8 Drawing Sheets

(51) Int. Cl.
  *A61M 5/20* (2006.01)
  *A61M 5/162* (2006.01)
  *A61M 5/142* (2006.01)
  *G06F 19/00* (2018.01)
  *H04W 12/08* (2009.01)
  *G06Q 50/24* (2012.01)

(52) U.S. Cl.
  CPC ....... *A61M 5/3202* (2013.01); *G06F 19/3468* (2013.01); *G06Q 50/24* (2013.01); *A61M 2005/208* (2013.01); *A61M 2205/3576* (2013.01); *A61M 2205/60* (2013.01); *G06Q 2220/00* (2013.01); *H04W 12/08* (2013.01)

(56) References Cited

U.S. PATENT DOCUMENTS

| | | | |
|---|---|---|---|
| 2006/0154642 A1* | 7/2006 | Scannell, Jr. | A01G 9/02 455/404.1 |
| 2009/0043253 A1 | 2/2009 | Podaima | |
| 2010/0026494 A1* | 2/2010 | Lees | G06K 7/0008 340/572.1 |
| 2013/0317753 A1 | 11/2013 | Kamen et al. | |

* cited by examiner

MEDICAL DEVICE SYSTEM AND METHOD FOR ESTABLISHING WIRELESS COMMUNICATION

This application is a Continuation of, and claims priority under 35 U.S.C. § 120 to, International App. No. PCT/DK2015/000001, filed 5 Jan. 2015, and claims priority therethough under 35 U.S.C. §§ 119, 365 to Danish App. Nos. PA 2014 00005, filed 8 Jan. 2014, and PA 2014 00175, filed 26 Mar. 2014, the entireties of which are incorporated by reference herein.

BACKGROUND

Field of Endeavor

The present invention relates to a system for establishing wireless communication between at least one medical device and at least one communication unit. The invention more particularly relates to a system for establishing wireless communication between at least one medical drug delivery device and at least one communication unit, where the system is provided to support generation of data associated with a patient's medicine administration in a seamless manner.

Brief Description of the Related Art

There is a general awareness that when taking medication it can be advantageous to collect data associated with such medicine intake procedures. Collection of such data is important for several reasons.

Medication adherence monitoring includes logging that the patient actually follows the dosing prescribed by his physician. Such monitoring is required in order to optimize the target drug concentration in the blood/body. The monitoring can additionally be of particular relevance for others parties such as the healthcare provider, who needs the information in order to ensure that the patient actually follows the recommended administration in such a way that the therapy will work optimally.

In addition, such logging of drug intake may be an advantage in preventing overdosing, in particular for patients likely to forget if and when the latest dose was taken and especially in therapies where overdosing may be critical for a patient, e.g., for very potent drugs. If overdosing occurs it may be beneficial for the patient himself to become aware of a potential hazardous situation but it could also be advantageous that remote caregivers and/or relatives become alerted to the situation so to be able to follow up on the patient's health.

Again in other situations it may be desirable to monitor situations of patients taking acute medication, e.g., a dose of Adrenalin following suspected anaphylaxis conditions, or a dose of Glucagon following suspected hypoglycemic event. In both of these examples, the acute dosing of medication may have dramatic positive effects on the patient's conditions but they do by no means provides any guarantee that the patient is now safe and as such able to independently consult with a physician and/or hospital for final clarification and care, if such is needed. For that reason information that such acute medication has been taken could preferably be transmitted to relevant remote caregivers and/or relatives to allow secondary procedures be initiated to eventually preserve the life of that particular patient which, e.g., would call not only for information that a dose has been given but, e.g., also current physical location of that patient upon activating the acute medicine dosing such that caregivers etc. may be able to locate the patient quickly as rescue delay may be critical in saving the patient's life.

In other situations the medicine dosing may be closely correlated with diagnostic measures obtained using other devices and equipment, e.g., a diabetic will regularly measure his blood glucose level and based on this adjust the amount of insulin to inject at a given point in time, e.g., also adjusted for parameters associated with expected food intake etc. Here a system supporting data, e.g., associated with dosed insulin, measured blood glucose and diet will help control the patient's disease and prevent, e.g., critical attacks of hypoglycemia.

Most commonly, data collection involving patients will typically require that the patient participate in assuring that the collection is properly carried out. It is known that the degree to which the patient has to actively act has a huge impact on the quality and regularity of the data acquired.

Since a majority of the patients are elderly, it is anticipated that they are much more technology adverse than the average person. Medical patients are often additionally challenged with an illness which makes them less flexible to learning and adhering to additional procedures, on top of the basic administration of the medicine itself, related to the acquisition of data associated with such administration.

Even if the patient is able to perform all required additional procedures associated with the acquisition of data, the patient might not want to do so, e.g., due to lack of motivation to invest the time required to carry through such procedures.

With respect to acute situations the patient might not be able to do anything else than merely focus on taking medication, despite being highly motivated and compliant to rules and procedures for such data acquisition procedures.

Accordingly, any system provided to support generating data associated with patient's medicine administration should ensure minimal burden on the patient and preferably act completely seamlessly and automatically in combination with the relevant dedicated medical drug delivery devices.

Thus, one of numerous aspects of the present invention includes a system configured to support generation of data associated with a patient's medicine administration completely seamlessly and automatically in combination with the relevant dedicated medical drug delivery devices.

Another aspect includes a system that can be used for providing interactive training of a user of a medical drug delivery device.

SUMMARY

Aspects of the present invention are explained in the following description and illustrated in the accompanying drawings.

Systems embodying principles of the present invention include a system for establishing wireless communication between at least one medical device having a predefined unique identification and at least one communication unit provided with a primary two-way wireless data communication interface comprising means for wirelessly performing primary two-way data communication including receiving and transmitting information, where the system comprises means for securing that the primary two-way wireless data communication can be carried out if and only if the communication unit positively and in advance has identified the predefined unique identification of the medical device. The system comprises secondary wireless communication means configured for carrying out identification of the predefined unique identification of the medical device through secondary wireless communication.

Hereby is achieved that the system can facilitate generation of data associated with a patient's medicine administration completely seamlessly and automatically in combination with the relevant dedicated medical devices. Moreover, a secure data transmission can be carried out.

The medical device may be a medical drug delivery device or another suitable type of medical device.

The medical device has a predefined unique identification, which may be of any type and may be provided in any suitable way. The unique identification may be provided as an electronic chip. A unique code may be pre-entered in the electronic chip. The unique identification may be a number or a visual pattern, e.g., a bar code or a QR code.

The communication unit provided with a primary two-way wireless data communication interface may be any suitable type of communication unit and the data communication interface may apply any suitable type of communication.

The means for securing that the primary two-way wireless data communication can be carried out if and only if the communication unit positively and in advance has identified the predefined unique identification of the medical device may be of any suitable type.

Since the primary two-way wireless data communication can be carried out if and only if the communication unit positively and in advance has identified the predefined unique identification of the medical device, a secure communication can be provided.

The system comprises secondary wireless communication means configured for carrying out identification of the predefined unique identification of the medical device through secondary wireless communication. The secondary wireless communication may be of any suitable type and may apply any suitable type of technology. The secondary wireless communication may be one-way wireless communication.

It may be an advantage that the wireless communication is a non-encrypted wireless communication and that the at least one communication unit is provided with a primary two-way secure wireless data communication interface comprising means for wirelessly performing secure primary two-way wireless data communication. The wireless communication may be one-way non-encrypted wireless communication.

Hereby it is possible to use simple and technically less demanding technology to provide verification of the predefined unique identification.

By using non-encrypted wireless communication it is possible to provide a cost beneficial solution that is easy to use and makes it possible to provide a system that can facilitate generation of data associated with a patient's medicine administration completely seamlessly and automatically.

It may be advantageous that the wireless data communication interface comprises means for wirelessly transmitting received information either processed or unprocessed to a remote recipient.

Hereby it is possible to communicate information to a healthcare personal such a physician.

The remote recipient may be any type of remote recipient such as relevant staff at a hospital, a physician, healthcare provider or a caregiver.

The information may be processed in any suitable way before it is sent to the remote recipient.

Data processing may involve compressing the data, calculation of statistical quantities and gathering various sets of data.

It may be an advantage that the communication unit comprises means for interpreting the unique identification and hereby unambiguously determine the type of the medical device on the basis of the unique identification.

Hereby the system is capable of automatically determining the type of the medical device. Accordingly, the system is capable of applying predefined information about the type of the medical device in order to determine the most appropriate assistance and/or guidance of the user of the medical device. Moreover, it is possible to send more specific and adjusted data to a remote recipient.

It may be beneficial that the secondary wireless communication means comprises a radio frequency interface configured to communicate radio frequency signals.

Hereby it is possible to provide radio communication in order to carry out identification of the predefined unique identification of the medical device. Accordingly, wireless transmission of signals can be used to provide the secondary wireless communication.

The secondary wireless communication means may be configured to receive a wireless radio frequency signal, e.g., sent by an electric chip provided in the medical device.

It may be advantageous that the secondary wireless communication means comprises an audio interface configured to receive an audio signal.

Hereby it is possible to use audio signals to carry out the secondary wireless communication.

It may be an advantage that the system applies easy, low-cost data protocols. By way of example, a QR code or a barcode may be read, e.g., by a smartphone camera that may carry static information such as the identification, e.g., a serial number. The cost added is negligible because such identification may be integrated into an existing medical device by means of labelling or a radio-frequency identification (RFID) device or a near field communication (NFC) device configured to establish radio communication between the medical device and the communication unit by bringing them into proximity.

It may be an advantage to provide communication between the medical device and the communication unit by means of an NFC device and an unpowered NFC chip.

It may be an advantage that a short range protocol is used to provide communication between the communication unit and the medical device.

It is possible to apply a wireless technology standard for exchanging data, preferably over short distances—e.g., those based on the several IEEE 802.15 standards, including, but not limited to, Bluetooth (e.g., Bluetooth Standard, low-energy, and Smart) and Zigbee, or the ANT and ANT+ protocols (Dynastream Innovations Inc., Cochrane, Canada). It may be an advantage to apply low-power radio-frequency transceiver chips.

The system may apply any suitable short range radio-frequency communication system which will allow for very flexible short range data exchange both from and to a medical device.

The communication unit may be a smartphone or another intermediate device that is configured to reach a remote recipients (e.g., over the Internet).

The use of a smartphone may require a pairing procedure to ensure patient data integrity. This may be acceptable for reusable medical devices. However, such procedure would be very cumbersome for a patient applying disposable devices, as pairing/initialization is required with every single device/use.

It is possible to apply any mobile communication standard such as Global System for Mobile Communications (GSM), the third generation (3G) Universal Mobile Telecommunications System (UMTS) standard, or the fourth generation (4G). The use of such a communication standard makes it possible to provide direct communication with, e.g., others which are Internet based. It may be beneficial to pre-pair a system using one of these communication standards with the telecommunication provider.

Some data and use situations may be supported by simple low-cost means whereas other situations need advanced data communication schemes. However, even if larger amounts of data are needed, the optimal data acquisition systems shall be designed to relieve the patient to the widest possible extent from any manual procedures required to facilitate such collection of data.

It may be an advantage that the system comprises a medical system application installed on a smartphone or another suitable device to act as a front end for a patient/user to collect or receive and transfer to a personal medical device which secures patient data privacy, e.g., through personal login with user name and password which is controlled with a central database to check validity of users attempting to enter the system.

Such system application may involve the step of reading a QR code, a barcode or another visual representation such as a label comprising a code of numbers and letters. The system application may also involve the step of determining an identification by using radio frequency identification (RFID) device or a near field communication (NFC) device and associate such static medical device information, e.g., with an event to be logged in the medical system application and/or in a remote server database.

It may be an advantage that the system comprises a medical system application that is furthermore capable of being set up to automatically connect with the medical device by means of a radio frequency technique (e.g., Bluetooth) and automatically import data without additional patient/user interaction. Hereby a user-friendly solution can be provided.

It may be an advantage that the system furthermore is capable of pairing with new devices (e.g., by using Bluetooth-communication) through simple device information contained in the form of, e.g., QR-code or other visual representations.

When the pairing has been conducted, a fully automating connection and import of more advanced data structures from the medical device (e.g., a disposable Bluetooth device) can be conducted so that operator uses barriers associated with setting up a secure wireless connection between system application and medical device are significantly reduced.

It may be an advantage that the system comprises means for preparing communication with an acute device holding information such that in an emergency situation the communication unit (e.g., a smartphone) acts as a wireless gateway for sending location information (e.g., GPS coordinates) of the user of the medical device to selected recipients.

It may be beneficial that the medical device comprises means for identifying the location information of the medical device, e.g., upon activation, and means to communicate such information to the communication unit (e.g., a smartphone) and/or alternatively to transmit such information over global communication systems to recipients, e.g., via a wireless protocol (e.g. GSM, 3G, 4G).

It may be beneficial that the device is configured to wake up when the user of the medical device activates the device.

It may be beneficial that the device is configured to wake up when the user of the medical device removes the needle protection cap (prior to injection) and/or activates the dose release by pressing down a dosing button and/or when a dose has been given by auto injector, e.g., following successful skin-sensor activation and depression of a dosing activation button and/or by manual switch placed on device exterior.

It may be advantageous that the device is configured to send relevant information to a recipient, including the date and time for activation and/or location information of the device upon activation and/or dose setting and/or detailed partial sequence steps with timestamp for every It may be beneficial that the secondary wireless communication means comprises an optical scanning member configured to detect a visual representation such as light, a symbolic code (e.g., a number), a label, a barcode, a quick response code or another image.

Hereby it is possible to provide a simple and efficient way of carrying out the secondary wireless communication.

A label may comprise numbers, letters or other symbols within a predefined area of symbols. It is possible to provide a label having a code that contains unique information about the type of the medical device and user specific data or information.

It may be an advantage that the secondary wireless communication means comprises a scanning member configured to detect electric capacitance and/or an electrical field and/or a magnetic field.

Detection of electric capacitance and/or an electrical field and/or a magnetic field may be provided by any suitable means.

Electrical capacitance may be determined by a display touch sensor. The scanning member may be configured to detect anything that is conductive or has a dielectric different from that of air.

The scanning member may be of any suitable type and may comprise means for detection of an electrical field. Such scanning member may include an electric field proximity sensor that is configured to detect changings in the electric field due to perturbations caused by the existence of a nearby object that is at least slightly conductive.

It may be advantageous that the secondary wireless communication means comprises a scanning member configured to detect vibrations.

The scanning member may comprise an accelerometer or a gyroscope. The accelerometer may be a single-axis or a multi-axis accelerometer configured to detect vibrations within any predefined area of magnitude and direction.

It may be an advantage that the communication unit comprises secondary communication means for sending at least one signal to the medical device in order to activate the medical device and that the medical device comprises means for receiving the at least one signal.

Hereby it is possible to apply the communication unit to "wake up" the medical device in order to initiate a validation process (such as determination of a unique identification) that involves that the medical device is activated.

It may be advantageous that the medical device comprises means for sending at least one response signal to the communication unit and that the communication unit comprises means for receiving the at least one response signal.

Hereby it is possible to activate the medical device and hereafter sending at least one response signal to the communication unit so that the unique identification of the medical device can be determined.

It may be beneficial that the medical device comprises means for logging and storing information about the use of the medical device.

Hereby it is possible to share this information with relevant personal such as healthcare staff, a physician or another remote recipient.

The means for logging and storing information may be of any suitable type and may involve means for associating a time stamp to each event (e.g., every time the medical device is used or every time a medication has been taken).

It is preferred that the medical device comprises means for automatically logging and storing information about the use of the medical device.

It may be an advantage that the medical device comprises an activation member that is configured to be triggered by mechanical activation of the activation member.

Hereby it is possible to trigger activation of a medical device when it is touched, moved or in any other way is exposed for a mechanical activation. Accordingly, the medical device may be kept in a "sleep mode" while not being used and afterwards the medical device may be activated due to a predefined mechanical action.

It may be advantageous that the medical device comprises secondary communication means for sending at least one signal to the communication unit upon the activation member being triggered.

Hereby the medical device sends a signal to the communication unit when the communication unit when its activation member has been triggered.

It may be preferred that the sending of the at least one signal is carried out in real time.

It may be advantageous that the medical device is a medical drug delivery device comprising a needle protection cap and means for wirelessly sending relevant information such as date and time for activation of the medical device and/or the location of the medical device upon activation of the protection cap.

Hereby it is possible to gather valuable information in case of a sudden activation (e.g., in an acute situation, in which a medical drug delivery device is activated). This information may be sent to relevant personal such as care givers.

It may be beneficial that the communication unit comprises a first primary communication means configured to transmit a first activation signal to the medical device and a second primary communication means configured to transmit a second activation signal to the medical device.

Hereby it is possible to provide a secure activation mechanism that requires that both a first activation signal and a subsequent second activation signals is sent in order to activate the medical device.

It may be an advantage that the communication unit comprises means for providing interactive training of a user of the medical device.

Hereby the communication unit can be used to provide device and user specific information interactively to the user.

The means for providing interactive training of a user of the medical device may be of any suitable type. The secure activation of the medical device opens up for allowing communication of user specific information, since the communication is only allowed if the communication unit positively and in advance has identified the predefined unique identification of the medical device.

It may be an advantage that the interactive training can be provided on a real-time basis.

It may be beneficial that the communication unit comprises means for deactivating the medical device when the communication unit is used for providing interactive training of a user of the medical device.

Hereby it is possible to use the medical device in to different modes. One "active mode" in which the medical device is capable of being used, and one "passive mode" in which the medical device is deactivated.

It may be advantageous that the communication unit comprises means for tracking and monitoring the behavior of the user and that the communication unit comprises means for providing interactive training of a user of the medical device, which interactive training depends on the behavior of the user.

Hereby it is possible to provide a user specific interactive training that is based on logged behavior of the user. Accordingly, the training may focus on elements that cause trouble for the user or elements that the user somehow may need more knowledge about.

Other aspects include a method for establishing wireless communication between at least one medical device having a predefined unique identification and at least one communication unit provided with a primary two-way wireless data communication interface comprising means for wirelessly performing primary two-way data communication including receiving and transmitting information, where the method comprises the step of securing that the primary two-way wireless data communication is carried out if and only if the communication unit positively and in advance has identified the predefined unique identification of the medical device. The method comprises the step of carrying out identification of the predefined unique identification of the medical device by using secondary wireless communication.

Hereby the method makes it possible to provide a way to support generation of data associated with patient's medicine administration completely seamlessly and automatically in combination with the relevant dedicated medical drug delivery devices.

It may be an advantage that the method applies a system as described herein.

BRIEF DESCRIPTION OF THE DRAWINGS

The invention will become more fully understood from the detailed description given herein below. The accompanying drawings are given by way of illustration only, and thus, they are not limitative of the present invention. In the accompanying drawings.

DETAILED DESCRIPTION OF EXEMPLARY EMBODIMENTS

Figure 1A:
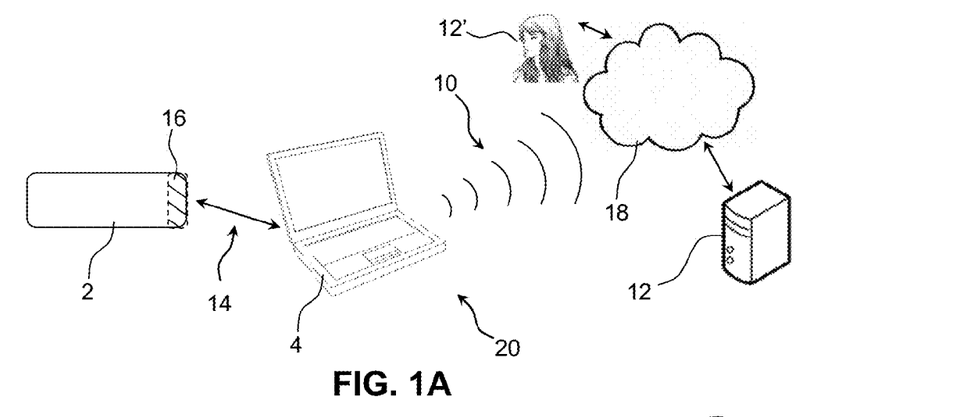
FIG. 1A shows a schematic view of a first system according to the invention.

Referring now in detail to the drawings for the purpose of illustrating preferred embodiments of the present invention, a schematic view of a system 20 according to principles of the invention is illustrated in FIG. 1A. The system 20 includes a medical drug delivery device 2 provided with an activation member 16 that is configured to activate the medical drug delivery device 2 when being axially displaced or mechanically stressed.

The medical drug delivery device 2 may be, e.g., a motorized syringe or an infusion pump.

The system 20 includes a laptop computer (communication unit) 4 that receives information 14 from the medical drug delivery device 2. The medical drug delivery device 2 has a predefined unique identification. The laptop computer 4 identifies the predefined unique identification of the medical device 2 by receiving the information 14.

The predefined unique identification of the medical device 2 may be integrated by means of an electronic chip within the medical device 2.

The laptop computer 4 includes a secondary one-way wireless communication module (not shown) configured for carrying out identification of the predefined unique identification of the medical device 2 through secondary one-way wireless communication, e.g., by means of radio frequency communication.

When the laptop computer 4 has identified the predefined unique identification of the medical device 2, the laptop computer 4 receives information 14 from the medical device 2. The laptop computer 4 sends information 10 to a remote recipient 12 and a caregiver 12'. The information 10 is sent wirelessly from the laptop computer 4 via the internet 18. The information 10 may contain an overview of the use of the medical device including time stamps. The information 10 is encrypted in order to provide a safe communication of information.

Figure 1B:
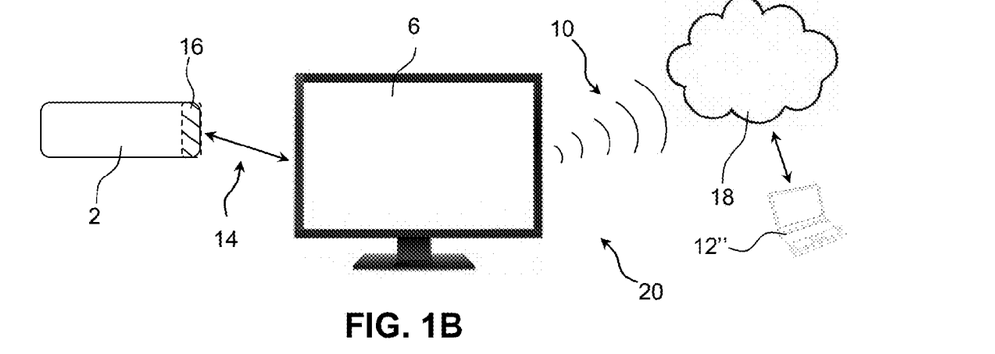
FIG. 1B shows a schematic view of a second system according to the invention.

FIG. 1B illustrates a schematic view of another system 20 according to principles of the invention. The system 20 includes a medical drug delivery device 2 that is configured to communicate with a television (communication unit) 6. An additional communication unit may be arranged to provide communication between the television 6 and the medical drug delivery device 2. The system 20 includes a medical drug delivery device 2 equipped with an activation member 16 that is configured to activate the medical drug delivery device 2 when being mechanically stressed, e.g., shaken, squeezed, etc.

When the medical drug delivery device 2 has been activated, a predefined unique identification of the medical device 2 can be detected by the television 6. When the predefined unique identification of the medical device 2 has been detected, the television 6 receives information logged within a storage device (e.g., memory, not shown) in the medical device 2. The received information is sent to a remote recipient 12" (a laptop) via the internet 18.

Figure 1C:
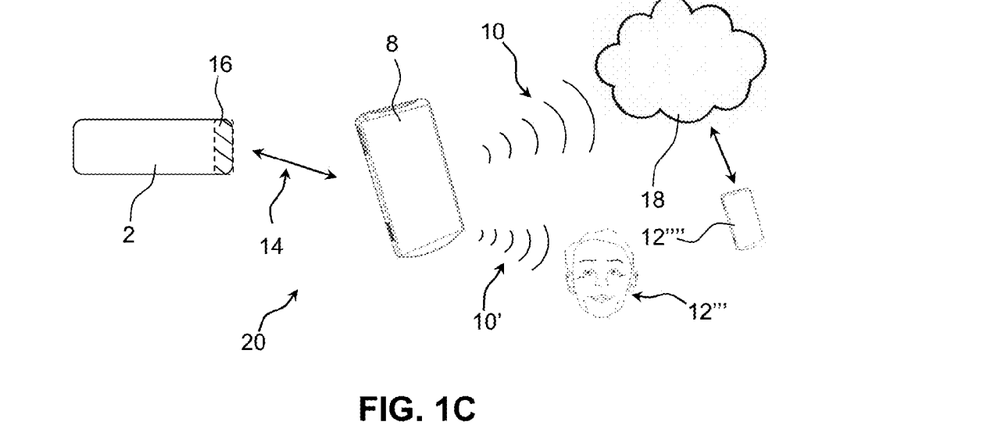
FIG. 1C shows a schematic view of a third system according to the invention.

FIG. 1C illustrates a schematic view of a system 20 according to principles of the invention. The system 20 includes a smartphone (communication unit) 4 receiving information 14 from a medical drug delivery device 2 provided with a predefined unique identification that is identified by the smartphone 8.

The predefined unique identification of the medical device 2 may be integrated by means of a label equipped with a bar code a QR code or another visual representation that may be detected and verified by means of a camera of the smartphone 8.

When the smartphone 8 has identified the predefined unique identification of the medical device 2, the smartphone 8 receives information 14 from the medical device 2 and the smartphone 8 sends information 10 to a first remote recipient (a physician) 12''' and information 10' to a smartphone of a healthcare person 12'''' via the internet 18. The information 10 may contain any suitable information of the use of the medical device 2.

Figure 2:
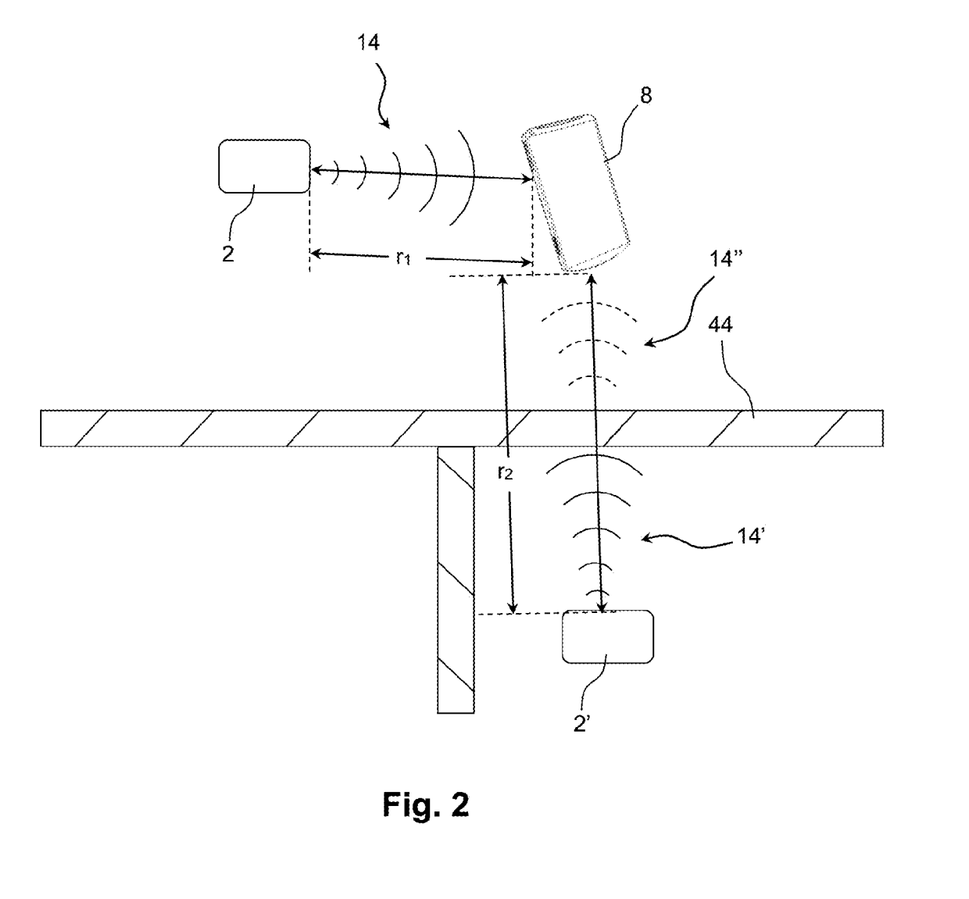
FIG. 2 shows an example of a security mechanism of a system according to the invention.

FIG. 2 illustrates an example of a security mechanism of a system according to principles of the invention. The system includes a communication unit in the form of a smartphone 8. The smartphone 8 is arranged in close proximity to a first medical device 2. The distance between the smartphone 8 and the first medical device 2 is r1.

In an adjacent room behind a wall 44, a second medical device 2' is arranged. The distance between the smartphone 8 and the second medical device 2 is r2. The distance r1 is significantly smaller than the distance r2.

In order to prevent unintended pairing of the medical device 2', the smartphone 8 is configured to identify the predefined identification of only the first medical device. This may be done by providing the smartphone with an application including information about the first medical device 2. When information 14 is received by the smartphone 8, the application within the smartphone 8 ensures that the smartphone 8 identifies the first medical device 2.

When the second medical device 2' sends information 14', 14" to the smartphone 8, the smartphone 8 will not recognize the information 14" sent by the second medical device 2'. Accordingly, since the unique identification of the second medical device 2' has not been identified, the primary two-way wireless data communication means (not shown) of the smartphone 8 will not receive logged information within the second smartphone 8.

The information 14, 14', 14" may be a coded radio-frequency signal. The information 14, 14', 14" may also represent visual detection of a label with a visual code, a bar code, a QR code or another visual representation.

If the information 14', 14" is an audio signal, it is possible to restrict the second medical device 2' from pairing with the smartphone 8 by measuring the amplitude (the sound level) of the audio signal. Since the distance r1 between the first medical device 2 and the smartphone 8 is short, the amplitude (the sound level) of the audio signal sent from the first medical device 2 may exceed a predefined lower sound level limit.

Since the distance r2 between the second medical device 2' and the smartphone 8 is larger than the distance r1, and since a wall 44 is provided between the second medical device 2' and the smartphone 8, the audio signal 14" received by the smartphone 8 is too weak to exceed the predefined lower sound level limit. Accordingly, it is possible to restrict the second medical device 2' from pairing with the smartphone 8.

Figure 3A:
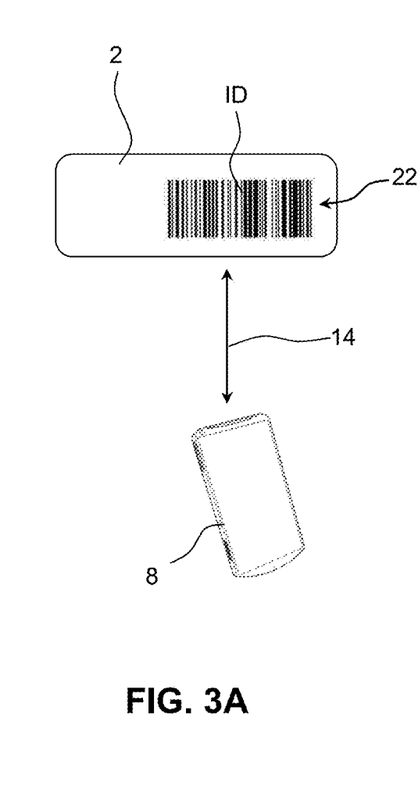
FIG. 3A shows an example of how information is communicated between the communication unit and a medical device.

FIG. 3A illustrates an example of how information 14 is communicated between a communication unit 8 (a smartphone) and a medical device 2. The smartphone 8 is used as a communication unit provided with an application configured to identify the unique identification ID of the medical device 2 on the basis of a detected barcode 22.

The bar code 22 may be read by using a camera (not shown) integrated in the smartphone 8. The unique identification ID may be provided as a label or by other means attached to the medical device 2. The bar code 22 may include information about the type of the medical device and about the user of the medical device 2.

Figure 3B:
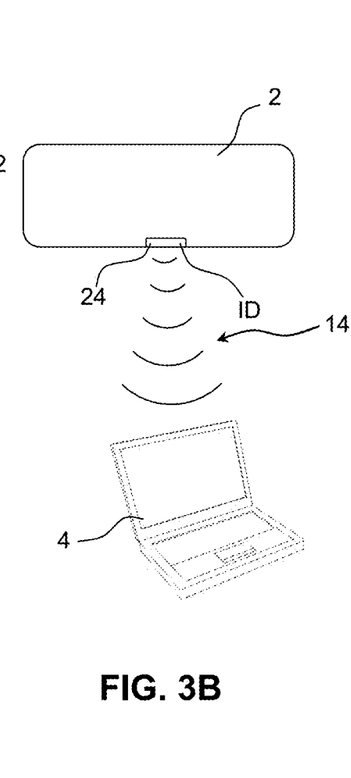
FIG. 3B shows another example of how information is communicated between the communication unit and a medical device.

FIG. 3B illustrates another example of how information 14 can be communicated between a communication unit 4 (a laptop) and a medical device 2. The laptop 4 is used as a communication unit configured to identify the unique identification ID of the medical device 2. The unique identification ID is detected by receiving a transmitted radio frequency signal 14. The radio frequency signal 14 is transmitted by a tag member 24 integrated in the medical device 2. The tag member 24 may be a NFC tag or RFID tag, by way of example, and the communication unit 4 includes a corresponding module which can wirelessly read the tag 24.

The unique identification ID is identified by the laptop 4 when the laptop 4 receives the radio frequency signal 14 transmitted by the tag member 24.

Figure 3C:
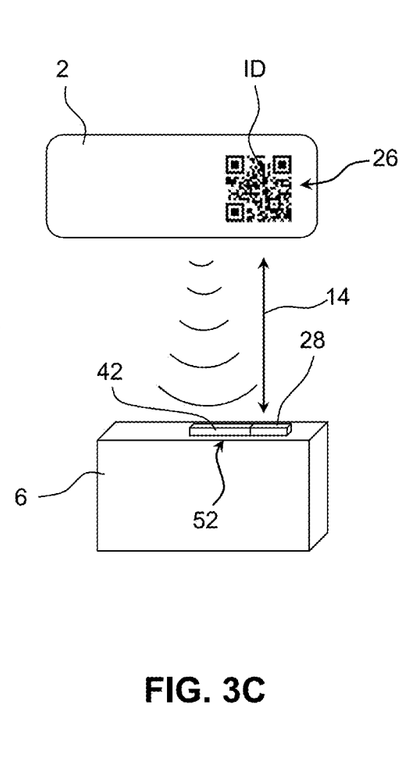
FIG. 3C shows a third example of how information is communicated between the communication unit and a medical device.

FIG. 3c illustrates another example of how information 14 can be communicated between a communication unit 6 and a medical device 2. The communication unit 6 is configured to identify the unique identification ID of the medical device 2. The unique identification ID is a QR code 26 provided at the outer surface of the medical device 2.

The communication unit 6 includes a communication interface 52 having a receiver member 42 configured to detect information transmitted by the medical device 2. The information may be radio frequency waves, infrared light or audio signals. The communication interface 52 includes a scanning member 28 configured to scan the QR code 28. The scanning member 28 may include a camera (not shown).

The communication unit 6 may be configured to require identification of both the QR code and additional signals (e.g., radio frequency signals transmitted by a NFC chip). It is possible to require that both signals are identified in order to permit the communication unit 6 to send information to a remote recipient (not shown).

Figures 4A, 4B, 4C:
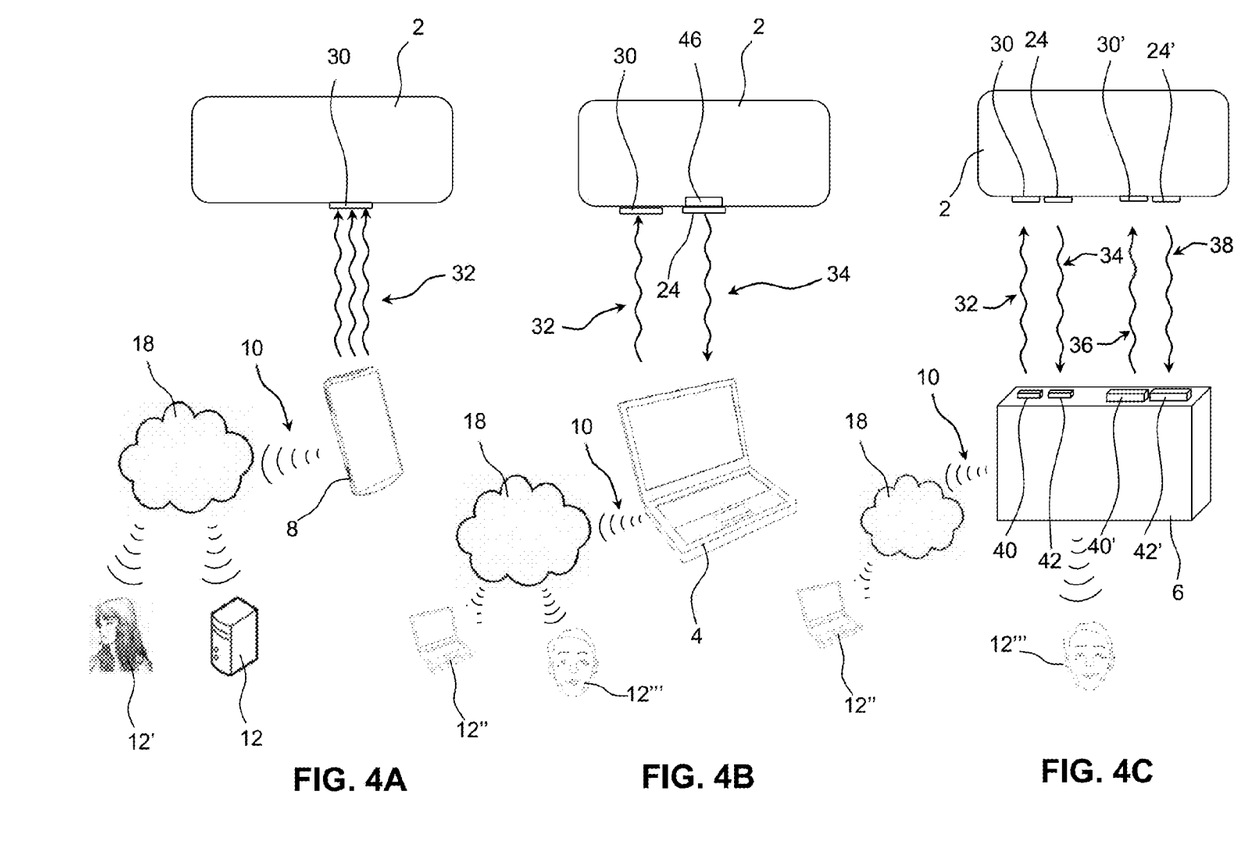
FIG. 4A shows an example of how a medical device is activated by means of a communication device.
FIG. 4B shows another example of how a medical device is activated by means of a communication device.
FIG. 4C shows a third example of how a medical device is activated by means of a communication device.

FIG. 4A illustrates a system according to principles of the invention. The system includes a smartphone 8 (communication unit) and a medical device 2 equipped with an activation member 30 configured to receive an activation signal 32 transmitted by a smartphone 8.

When the activation signal 32 is received by the medical device 2, the smartphone 8 may identify the unique identification of the medical device 2 by using any suitable communication means. Hereafter the smartphone 8 may receive information/data logged within storage media of the medical device 2 and send the information/data to a remote recipient 12 (a server) or a caregiver 12'. Information 10 may be sent to these remote recipients 12, 12' via the Internet 18.

FIG. 4B illustrates another system according to principles of the invention. The system includes a laptop 4 (communication unit), and a medical device 2 equipped with an activation member 30 configured to receive an activation signal 32 transmitted by a smartphone 8. The medical device 2 is equipped with a tag member 24 configured to transmit radio frequency signal (a response 34) to the laptop 4. The medical device 2 includes a data storage 46 configured to contain data.

When the activation signal 32 is received by the medical device 2, the laptop 4 may identify the unique identification of the medical device 2, e.g., by receiving a response signal 34 transmitted by the medical device 2. Hereafter, the laptop 4 is ready to receive data stored in the data storage 46 of the medical device 2.

The logged data received by the laptop 4 is transmitted towards two remote recipients 12 (a laptop 12") or a physician 12'''. The information 10 is transmitted to the remote recipients 12, 12' via the Internet 18.

FIG. 4C illustrates a system according to principles of the invention. The system includes a box-shaped communication unit 6, and a medical device 2 equipped with a first activation member 30, a first tag member 24, a second activation member 30', and a second tag member 24'.

Activation of the medical device 2 requires activation of both the first activation member 30 and the second activation member 30'. Hereby a safe activation procedure is achieved.

A first activation signal 32 is transmitted by the first transmission member 40 of the communication unit 6 and received by the first activation member 30 of the medical device 2. A second activation signal 36 is transmitted by the second transmission member 40' of the communication unit 6 and received by the second activation member 30' of the medical device 2.

A first response signal 34 and a second response signal 38 is transmitted from the medical device 2 and received by the receiving members 42, 42' of the communication unit 6.

When the activation signal 32 is received by the medical device 2, the laptop 4 may identify the unique identification of the medical device 2, e.g., by receiving a response signal 34 transmitted by the medical device 2. Hereafter the laptop 4 is ready to receive data stored in the data storage 46 of the medical device 2.

The communication unit 6 communicates with a computer 12" via the Internet 18. The communication unit 6 communicates with a physician 12'''.

Figure 5:
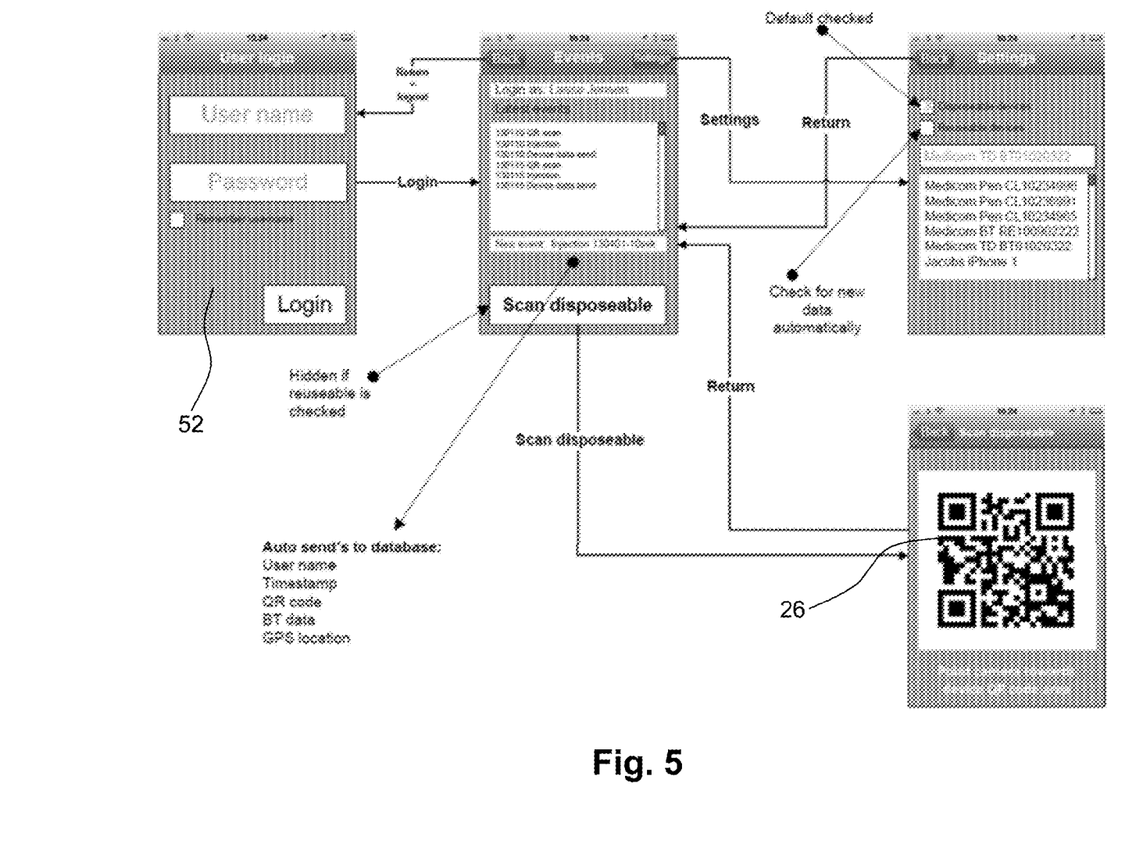
FIG. 5 shows a schematically view of a medical system application according to the invention.

FIG. 5 schematically illustrates a view of a medical system application installed on a personal smartphone to act as a front end for a user to collect or receive and transfer information to a personal medical device. It is important to underline that the system according to principles of the invention secures patient data privacy. This may be achieved through personal login with a user name and password like that illustrated in FIG. 5. The personal login is controlled by a central database (not shown) in order to check the validity of users attempting to enter the system.

The medical system application is able to read QR codes, bar-codes, or alternatively, radio frequency signals from RFID devices or NFC devices and associate such static medical device information, e.g., with an event to be logged in the medical system application and/or in a remote server database.

The medical system application is furthermore capable of being set up to automatically connect with, e.g., Bluetooth low-energy devices and automatically import data without additional patient/user interaction.

The medical system application may be capable of pairing with new Bluetooth devices through simple device information contained in, e.g., QR-code thereby fully automating connection and import of more advanced data structures from disposable Bluetooth devices. In this way the operator use barriers, e.g., associated with setting up secure wireless connection between the system application and the medical device, is thereby significantly reduced.

Figure 6:
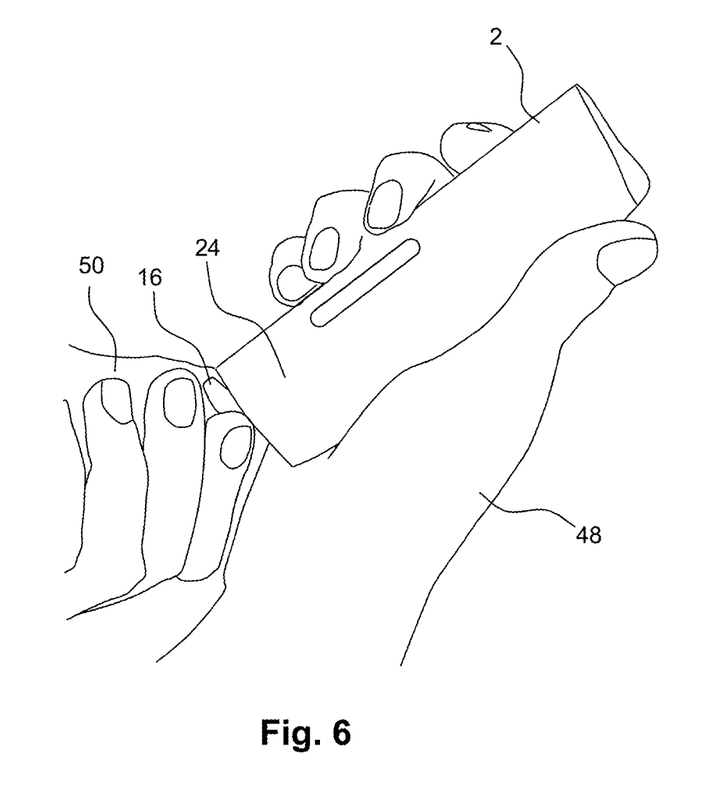
FIG. 6 shows an example of how a medical drug delivery device is activated.

FIG. 6 illustrates an example of how a medical drug delivery device 2 can be activated. The medical drug delivery device 2 is held in the hands 48, 50 of a user of the medical drug delivery device 2. The medical drug delivery device 2 includes a tag member 24 configured to wirelessly communicate with a communication unit (not shown).

The medical drug delivery device 2 includes an activation member 16 provided at the distal portion of the medical drug delivery device 2. When the activation member 16 is moved, the medical drug delivery device 2 is activated. When the medical drug delivery device 2 has been activated, the unique identification of the medical drug delivery device 2 can be identified by a communication unit (not shown).

Communication between the medical drug delivery device 2 and a communication unit (not shown), e.g., a smartphone, may be carried out by any suitable protocol such as Bluetooth. In an emergency situation the smartphone and a system application (e.g., like the one illustrated in FIG. 5) may conveniently act as a wireless gateway for sending, e.g., GPS coordinates of patient location to selected recipients.

The medical drug delivery device 2 may contain electronic components configured to identify position information (e.g., the GPS location), e.g., upon activation, and means to communicate such information to a smartphone application and/or alternatively to transmit such information over global communication systems to recipients, e.g., via GSM, 3G, 4G, or other suitable wireless protocols.

Figures 7A, 7B:
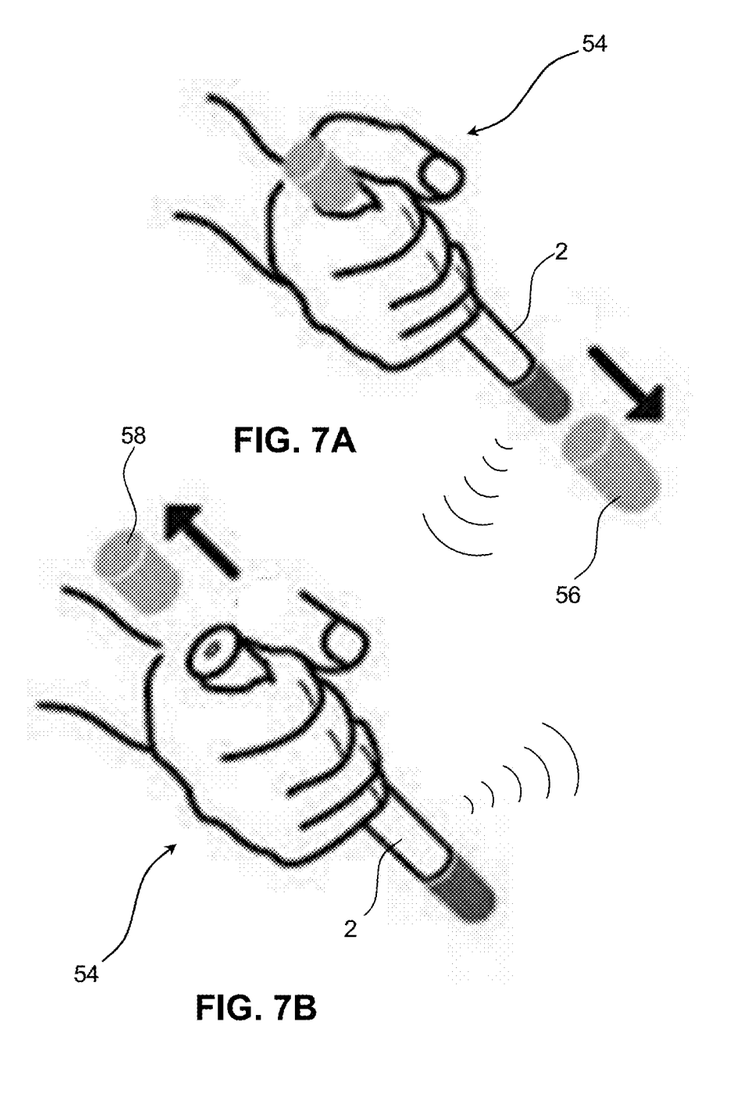
FIG. 7A shows an example of how a medical drug delivery device is activated.
FIG. 7B shows another example of how a medical drug delivery device is activated.

FIG. 7A illustrates another example of how a medical drug delivery device 2 is activated. The medical drug delivery device 2 wakes up when the user 54 of the medical drug delivery device 2 activates it. The medical drug delivery device 2 is activated by removing the needle protection cap 56 (prior to injection).

The medical drug delivery device 2 is configured to send relevant information to a recipient (e.g., a communication unit). Such data may include date and time for activation, and GPS location of the medical drug delivery device 2 upon activation. The data may also include dose setting or detailed partial sequence steps with timestamp for every step.

FIG. 7B shows another example of how a medical drug delivery device 2 is activated. The medical drug delivery device 2 wakes up when the user 54 of the medical drug delivery device 2 activates it, e.g., by activating a dose release by pressing down a dosing button 58 or when a dose has been given by auto injector, e.g., following successful skin-sensor activation and depression of dosing activation button and/or by a manual switch placed on device exterior.

The medical drug delivery device 2 is adapted to send relevant information to a recipient such as a communication unit. Accordingly, data including date and time for activation, and GPS location of the medical drug delivery device 2 may be communicated to a communication unit.

Figure 8A:
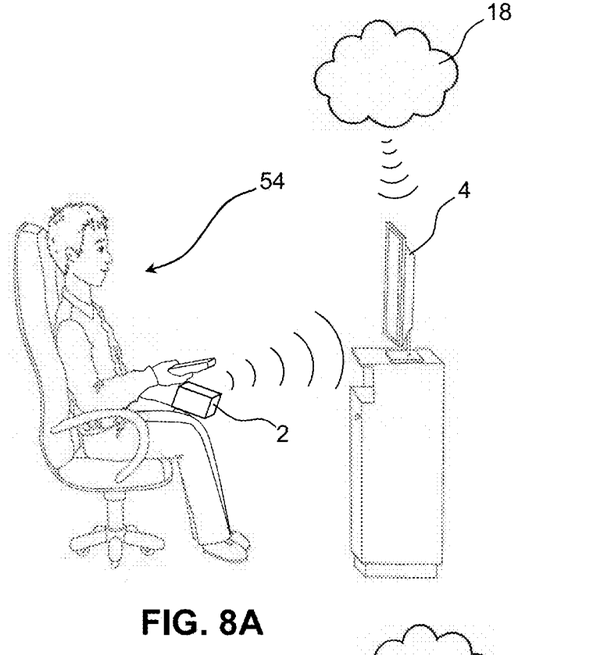
FIG. 8A shows a first example of a user of a medical device performing interactive training by using a system according to the invention and FIG. 8B shows a second example of a user of a medical device performing interactive training by using a system according to the invention.

FIG. 8A illustrates a first example of how a user 54 of a medical device 2 can perform interactive training by using a system according to principles of the invention. The user 54 of the medical device 2 rests in a chair in front of a television 4 that functions as communication unit. The television 4 receives information wirelessly from the Internet 18, while communication is established between the medical device 2 and the television 4.

Due to a prior identification of the unique identification of the medical device 2, the television has "knowledge" about the type of medical device 2 and hereby the television 4 is capable of receiving appropriate information from the Internet 18. Identification of the unique identification of the medical device 2 may initially be carried out by pairing the medical device 2 and the television 4, e.g., by using Bluetooth-communication. The pairing may be accomplished by means of any suitable type of secondary communication, e.g., radio frequency communication.

Figure 8B:
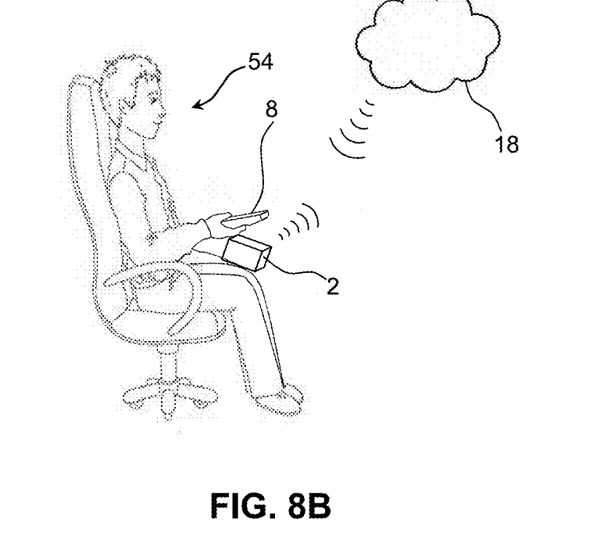

FIG. 8B illustrates another example of a user 54 of a medical device 2 performing interactive training by using a system according to principles of the invention.

The user 54 of the medical device 2 rests in a chair and has a medical device 2 as well as a smartphone 8 in his hands. The smartphone 8 receives wireless information from the Internet 18. Wireless communication is established between the medical device 2 and the smartphone 8.

Since the unique identification of the medical device 2 has been identified by the smartphone 8, the smartphone 8 "knows" what type medical device 2 the user 54 is applying. For the same reason the smartphone is capable of receiving appropriate information (including device specifications) about that specific medical device 2 from the Internet 18.

Accordingly, an optimal interactive training may be provided by using a system according to the invention.

Many new designs include electronics and connectivity with the ability to detect internal, e.g., auto injector, status modes and relay such information to a peripheral (connected) device. Connection to a peripheral device need not be wireless and even the connection of, e.g., a USB connector will act as a signal to the drug delivery device that in this scenario it will not give any medication but only act as a training device.

With wireless connection the user 54 has to manually select a special training mode in which the normal functions may be limited in acting the role as a training device.

When connected to peripheral device and acting as an interactive training device, the drug delivery device will not give any medication, but instead log, e.g., all button presses (activation, skin-sensor, syringe detection, etc.) and send info to a peripheral device and in accordance with progression and interaction from the user, the peripheral device will, e.g., show video sequences to more clearly demonstrate the proper handling of the device.

Alternatively the peripheral device may coordinate the input from the drug delivery device to control a game application which focuses on individual stepwise user operation sequences.

It is possible to track and monitor the user's behavior and performance and potentially adaptively focus training in certain areas of the user 54 operation cycle and/or provide performance feedback to a user 54, caregiver, clinician or a device manufacturer.

For drug delivery devices without any electronics an additional training module to interact with the mechanical device is still possible. It may be relevant for low-cost acute therapies of adrenaline auto injectors, which would effectively achieve the same as with electronic.

In one embodiment of a system according to principles of the invention, when a user starts on a treatment, there could be a supervision phase of a time period such as a couple of weeks, where, e.g., the caregiver gets confirmation from the medical device 2, that the injections were done successfully and straight forward according to the user instructions.

The training functionality of the medical device 2 may incorporate speech synthesis and a loudspeaker, so that the device itself could guide the user 54 also during an injection.

Generally, the system according to principles of the invention may include a communication unit 4, 8 that is capable of acting as a user interface for interactive training where wireless connection to medical device relays real-time data on, e.g., button activations etc., which in combination with audio-visual information on a system application that establishes a simulated use, very close to real use, and where issues connected with easy wirelessly connecting the medical device 2 to the system application is maintained in a highly patient friendly manner, e.g., based on simple scanning of a medical device QR-code after which full, e.g., Bluetooth low-energy connection is operational.

QR-codes may contain links to the latest update from the manufacturer of training with specific medical device and links to video instructions relevant for such training.

A system application may hold features to log user training that has taken place, e.g., at regular intervals, e.g., relevant for acute use medical drug delivery devices 2 where the device is used very rarely and potentially never and where a user 54 may never obtain confidence with correct use through other means of, e.g., initial face to face training by clinical personal or other caregivers.

A medical system application according to principles of the invention may be installed on a personal smartphone 8, a television 4, or any other appropriate type of communication unit. The communication unit will be able to facilitate connection from a medical device 2 and thereby allow flexible communication of data between the medical device 2 and data servers via, e.g., the Internet data infrastructure and from there interface to suitable, e.g., web-frontends and towards multiple type of users.

A personal smartphone 8 will typically be well integrated with the Internet data infrastructure but the wireless interfacing to medical devices 2 or various different kinds, and both reusable but also single use devices, is knows to be challenging as, due to patient data privacy, an encrypted data connection is required which in terms require separate user controlled pairing procedures which may be cumbersome for the average user to perform practically.

By easing up such individual pairing procedures in order to facilitate more advanced and flexible wireless data communication through utilizing a more simple unique and 'machine' readable information, such as QR-code of barcodes read by smartphone camera, or RFID or NFC read by smartphone built-in technology, to automate such pairing, the acceptability of such connected data systems to support medical therapies will be much more acceptable and adaptable thereby removing known operator barriers and hence support improved medical treatment.

Systems according to principles of the invention may establish patient data safe advanced wireless connection in several different ways. For a relevant medical therapy it holds value for the safety and efficacy that key parameters associated with the drug preparation and administration is acquired as part of the drug delivery process in the hands 48, 50 of the user 54, e.g., in a home environment setting where, e.g., no clinical assistance is available to handle more subtle technical operation, hence all procedures shall be handled by the user 54.

In order to acquire such central parameters, the medical drug delivery device 2 according to principles of the invention may be equipped with electronics which either are also active during drug delivery (e.g., an injection process controlled by an electrical motor) or which is solely responsible for such parameter collection during an otherwise fully manual/mechanical drug delivery process.

Such a medical drug delivery device 2 may be single use or multiple use depending on a vast many criteria, ranging, e.g., from procedural complexity and to maximum allowable cost of treatment. During use, the medical drug delivery device 2 will automatically facilitate enabling of electronics to open for simple and/or advanced wireless communication when the secure path to a trusted secondary device (data recipient) has been established.

As part of the total drug administration process, before, during, or after drug delivery has been completed, the device will need to wirelessly offload acquired process parameters and in that attempt rely on establishing a secure wireless to a trusted host device, e.g., in the shape of the user's personal smartphone 8. Secure wireless communication may now be established in various different ways but where a common approach is, that a safe advanced wireless communication is facilitated by initial simple communication from the device to the smartphone 8.

The main risks associated with establishing the more flexible/advance wireless connection are that of accidentally (or by wrongful intent) obtain access to data that does not belong to that particular user, e.g., clearly foreseeable when in a nursing home (or a home with multiple patients), where a medical drug delivery device 2 can get connected to the wrong user's smartphone application if there is no control mechanism that ensures that only exactly that user's smartphone application connects for advanced data exchange with the same users medical drug delivery device 2.

A system according to principles of the invention may apply any sound representation to be picked up by either of a smartphone's microphones—anticipating the medical device to issue a characteristic sound sample (e.g. using DTMF tones similar to telephone dial signals or another characteristic and interpretable signal) and understood to uniquely identify the device in front of the patient's smartphone application.

Any information provided over electrical pads in the medical device capable of interfacing through a capacitive sensitive touch screen of the typical smartphone, e.g., by placing the device on top of the smartphone display and allowing for the smartphone application to interpret characteristic pad-location sequences to uniquely identify the medical device for the smartphone and hence allow opening for more flexible but encrypted wireless communication.

The sound representation may be a sequence of tones of various frequencies and duration. Moreover these sequences may be interrupted by predefined periods of silence. When the sound representation is picked up, the detected sound representation "signal" may be processed in any suitable way, e.g., a filtering process.

During the time when a medical device 2 is attempting to connect to the user's communication unit (e.g., a smartphone) the medical device 2 may issue, e.g., a characteristic light (to be picked up by smartphone camera or ambient light sensor) or a sound (to be picked up by smartphone microphones) containing a coded sequence characteristic to that particular device, e.g., by containing information of a device serial number, e.g., as an example but not limited to, as Morse code sequence or for sound signals using DTMF telephone dial tones. Such signals may be picked up by the user smartphone over a limited distance, e.g., when both the smartphone and the device are placed on the same table but not, e.g., across walls and hence any such connection will guarantee the connection between correct device and smartphone. Also a combination of light and sound codes may prove relevant for such simple interfacing.

In one embodiment of a system according to principles of the invention, during operation of the medical drug delivery device 2, the medical drug delivery device 2 may at a certain point in time begin broadcasting a signal over any suitable wireless communication protocol (e.g., "Wi-Fi") giving notice via the user's smartphone application to accept an attempt to connect to a medical device either by manually entering the device serial number thereby enabling a safe encrypted secondary wireless connection.

Alternatively, if regulations for level of user data privacy can tolerate this, the user may simply accept a request to connect by simply pressing a button and, i.e., not entering/ securing the identity of the medical device.

The concern for such methods is that other devices not physically present and visible to the user may generate such beacon signals thereby prompting the user to accept connection and only if the user can actively verify the identity of the device attempting connection will the user be sure that data communication is established in a safe manner.

To overcome concern if connecting to the appropriate medical device, a "Wi-Fi Beacon method" might be combined with other sensing means, e.g., designing the medical device to issue another physical signal (beeping, blinking, etc.) and have the same rhythm be represented on the user's smartphone display, so that if the patient sees a displayed sequence in sync with the device physical signal, then this raises the confidence for pairing to the correct device.

It may be an advantage that the smartphone includes a Wi-Fi card allowing an electronic device to exchange data or connect to the internet wirelessly.

It may be beneficial that the smartphone includes a radio frequency chip allowing the smartphone to transmit and receive radio frequency signals in order to deploy high-speed wireless technologies.

It may be an advantageous that the smartphone includes a touch display (e.g., a capacitive sensitive touch screen) and storage media suitable for receiving and storing data including programs (application software).

LIST OF REFERENCE NUMERALS 2, 2' Medical device
4 Communication unit
6 Communication unit
8 Communication unit
10, 10' Information
12, 12', 12" Recipient
12''', 12'''' Recipient
14, 14', 14" Information
16 Activation member
18 Internet
20 System
22 Bar code
24, 24' Tag member
26 Quick Response (QR) code
28 Scanning member
30, 30' Activation member
32 Activation signal
34 Response signal
36 Activation signal
38 Response signal
40, 40' Transmission member
42, 42' Receiving member
44 Wall member
46 Data storage
48, 50 Hand
52 Communication interface
54 User
56 Needle cap
58 Dosing button
ID Unique identification
r1, r2 Distance While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

That which is claimed is:

1. A system for establishing wireless communication between at least one medical device having a predefined unique identification (ID) and at least one communication unit having a primary two-way wireless data communication interface, the system comprising:

means for wirelessly performing primary two-way data communication including receiving and transmitting information between the medical device and the communication unit;

secondary one-way wireless communication means for communicating the predefined unique identification (ID) of the medical device through the secondary one-way wireless communication, wherein the secondary one-way wireless communication means includes means for non-encrypted wireless communication, and the means for wirelessly performing primary two-way data communication comprises an encrypted secure primary two-way wireless data communication interface;

means for ensuring that the primary two-way wireless data communication can be carried out if and only if the communication unit positively and in advance has identified the predefined unique identification (ID) of the medical device;

wherein the medical device comprises an activation member that is configured to be triggered by mechanical activation of the activation member, and secondary communication means for sending at least one signal to the communication unit upon the activation member being triggered, wherein the secondary one-way wireless communication means is for sending the at least one signal in real time, whereby the medical device is activated and sends at least one response signal to the secondary one-way wireless communication means to determine said predefined unique identification of the medical device; and wherein the communication unit comprises means for providing interactive training of a user of the medical device on a real-time basis.

2. A system according to claim 1, wherein the secondary wireless communication means comprises a radio frequency interface configured to communicate radio frequency signals.

3. A system according to claim 1, wherein the secondary one-way wireless communication means comprises an optical scanning member configured to detect a visual representation selected from the group consisting of light, a symbolic code, a label, a barcode, a quick response code, or an image.

4. A system according to claim 1, wherein the secondary one-way wireless communication means comprises a scanning member configured to detect electric capacitance and/or an electrical field and/or a magnetic field and/or vibrations and/or audio signals.

5. A system according to claim 1, wherein:
the communication unit comprises secondary communication means for sending at least one signal to the medical device in order to activate the medical device; and
the medical device comprises means for receiving the at least one signal.

6. A system according to claim 1, wherein the medical device comprises means for logging and storing information about the use of the medical device and the information communicated between the medical device and the communication unit when the communication unit has positively identified the predefined unique identification (ID) of the medical device.

7. A system according to claim 1, wherein the medical device is a medical drug delivery device comprising:
a needle protection cap and/or a dosing button and/or a skin sensor and/or a manual switch;
means for wirelessly sending information for activation of the medical device and/or the location of the medical device upon activation of the protection cap and/or upon activation of the dosing button and/or upon activation of the skin sensor and/or upon activation of the manual switch;
wherein the medical device is configured to send a signal to the communication unit upon the activation member being triggered; and
wherein the secondary communication means for sending at least one signal is for sending the at least one signal in real time upon activation of the protection cap.

8. A system according to claim 1, wherein the medical device is configured to send information to relevant personnel in case of sudden activation of the medical device.

9. A system according to claim 1, wherein the communication unit is configured to interpret the unique identification and unambiguously determine the type of the medical device based on the unique identification (ID).

10. A system according to claim 1, wherein the communication unit is configured to track and monitor the behavior of the user operating the medical device.

11. A system according to claim 1, wherein the communication unit comprises means for selecting a special training mode thereby limiting at least some of the functions of the medical device.

12. A system according to claim 1, wherein the communication unit comprises means for providing interactive training of a user of the medical device, which interactive training depends on the behavior of the user.

* * * * *